United States Patent [19]

Winterfeldt et al.

[11] Patent Number: 5,140,106
[45] Date of Patent: Aug. 18, 1992

[54] PROCESS FOR THE PRODUCTION OF 3-DEOXY-4-ENE STEROIDS

[75] Inventors: Ekkehard Winterfeldt, Iserhagen; Ulf Tilstamm, Hanover; Helmut Hofmeister; Henry Laurent, both of Berlin, all of Fed. Rep. of Germany

[73] Assignee: Schering Aktiengesellschaft, Berlin & Bergkamen, Fed. Rep. of Germany

[21] Appl. No.: 646,750
[22] PCT Filed: Mar. 8, 1990
[86] PCT No.: PCT/DE90/00183
§ 371 Date: Oct. 19, 1990
§ 102(e) Date: Oct. 19, 1990
[87] PCT Pub. No.: WO90/11290
PCT Pub. Date: Oct. 4, 1990

[30] Foreign Application Priority Data

Mar. 21, 1989 [DE] Fed. Rep. of Germany ....... 3909770

[51] Int. Cl.$^5$ .............................. C07J 7/00; C07J 9/00
[52] U.S. Cl. .................... 552/607; 552/540; 552/543; 552/544; 552/552; 552/553; 552/554; 552/555; 552/557; 552/599; 552/603; 552/605; 552/608; 552/610; 552/611; 552/650; 552/651
[58] Field of Search ............... 552/540, 557, 603, 605, 552/607, 611, 610, 608, 599, 650, 651, 539, 543, 544, 552, 554, 555, 553

[56] References Cited

U.S. PATENT DOCUMENTS 3,099,656 7/1963 Zderic et al. .................... 552/557
3,471,531 10/1969 Hughes et al. .

FOREIGN PATENT DOCUMENTS 0034114 8/1981 European Pat. Off. .
2158837 5/1972 Fed. Rep. of Germany .
39-17924 8/1964 Japan .................... 552/605

OTHER PUBLICATIONS

Gribble, Gordon, W., et al. "Reactions of Sodium Borohydride in Acidic Media; IV. Reduction of diarylmethanols and triaylmethanols in Trifluoroacetic acid." *Synthesis.* No. 3, pp. 172–176 (1977).

Gribble, Gordon W., et al. "Reactions of Sodium Borohydride in Acidic Media; VII Reduction of Diaryl Ketones in Trifluoroacetic Acid." *Synthesis,* No. 10, pp. 763–765 (1978).

Chemical Abstracts 100:94990n (Mar. 13, 1989).

*Primary Examiner*—Howard T. Mars
*Assistant Examiner*—Kimberly J. Kestler
*Attorney, Agent, or Firm*—Millen, White & Zelano

[57] ABSTRACT

A process for the production of 3-deoxy-4-ene steroids of the general formula I

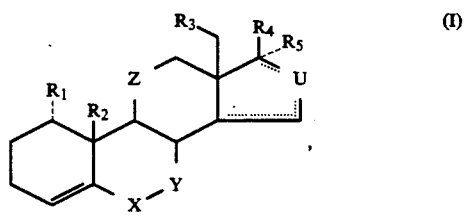

is described, in which $R_1$, $R_2$ and $R_3$ mean a hydrogen atom or a methyl group, $R_4$ represents a lower alkyl group, a phenyl group or a free, esterified or etherified hydroxy group, $R_5$ symbolizes a hydrogen atom, a vinyl group or the grouping —C≡$CR_6$ with $R_6$ meaning a hydrogen atom, an alkyl group with a maximum of 4 carbon atoms or a halogen atom, X represents a methylene group, a fluoromethylene group, an ethylidene group or a vinylidene group, Y and U represent a methylene group or an ethylidene group and Z symbolizes a methylene group, an ethylidene group, a vinylidene group, a chloromethylene group or a hydroxymethylene group and in which the bonds ⋯ represent three single bonds or one double bond and two single bonds or a conjugated double bond.

12 Claims, No Drawings

PROCESS FOR THE PRODUCTION OF 3-DEOXY-4-ENE STEROIDS

SUMMARY OF THE INVENTION

The invention relates to a process for the production of 3-deoxy-4-ene steroids of the general formula I

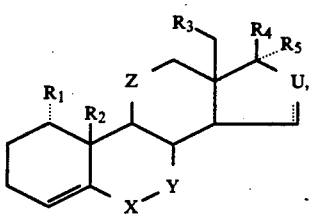

in which

R$_1$, R$_2$ and R$_3$ mean a hydrogen atom or a methyl group,

R$_4$ represents a lower alkyl group, a phenyl group or a free, esterified or etherified hydroxy group, R$_5$ symbolizes a hydrogen atom, a vinyl group or the grouping —C≡CR$_6$ with R$_6$ meaning a hydrogen atom, an alkyl group with a maximum of 4 carbon atoms or a halogen atom, X represents a methylene group, a fluoromethylene group, an ethylidene group or a vinylidene group, Y and U represent a methylene group or an ethylidene group and Z symbolizes a methylene group, an ethylidene group, a vinylidene group, a chloromethylene group or a hydroxymethylene group and in which the bonds ⋯ represent three single bonds or one double bond and two single bonds or a conjugated double bond, which is characterized in that a 3-oxo-4-ene steroid of the general formula II

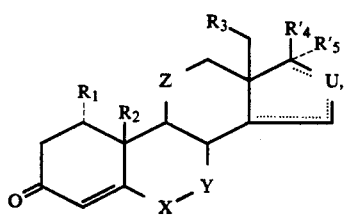

in which ⋯

R$_1$, R$_2$, R$_3$, X, Y, Z and U have the above-mentioned meaning and R'$_4$ and R'$_5$ mean the same as R$_4$ and R$_5$ or together represent an oxy group, is reduced with a reaction mixture of trifluoroacetic acid or trichloroacetic acid, optionally of another carboxylic acid and sodium borohydride.

3-deoxy-4-ene steroids of the general formula I, as is known, are pharmacologically effective substances or valuable intermediate products for the production of pharmacologically effective compounds (DE-A 2 361 120; EP-B 17 094 and EP-B 34 114).

Thus, for example, 3-deoxy-4-ene steroids of the general formula Ia

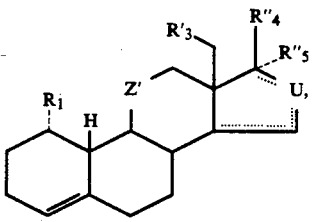

in which

R'$_3$ represents a hydrogen atom or a methyl group,

R''$_4$ represents a hydroxy group or an alkanoyloxy group with up to 4 carbon atoms, R''$_5$ represents a hydrogen atom, a vinyl group, an ethinyl group, a chloroethinyl group or a 1-propinyl group, ⋯

Z symbolizes a methylene group or a vinylidene group,

U represents a methylene group, and means a single bond or a double bond, are marked by a strong gestagen effectiveness. Examples of such gestagenally effective steroids are lynestrenol (17alpha-ethinyl-4-estren-17beta-ol) and desogestrel (17alpha-ethinyl-18-methyl-11-methylene-4-estren-17beta-ol).

According to the known prior art, the 3-deoxy-4-ene steroids of the general formula I are produced from the 3-oxy-4-ene steroids of the general formula I so that the latter, for example, are converted by ethanedithiol to 3-thioketals and in the latter the thioketal group is cleaved by sodium or lithium in liquid ammonia. This process is quite expensive because of the high energy costs spent and further has the drawback that it is very harmful to the environment because of the very offensive odor.

In contrast, the process according to the invention is a single-stage reaction, simple to perform, and with little harm to the environment, in which, just as in the previously known two-stage process, yields of about 60 to 85% of theory are achieved.

The process according to the invention is suitably performed so that primarily the sodium borohydride is reacted at a temperature of −10° C. to +20° C. in the trifluoroacetic acid or trichloroacetic acid and optionally another carboxylic acid. Since in this case, a great foam formation takes place as a result of generation of hydrogen, acetonitrile is suitably added to the trihaloacetic acids before the beginning of the reaction, by which the foam formation is largely suppressed. When trifluoroacetic acid is used it is necessary, with the use of trichloroacetic acid it is not always necessary to add additional carboxylic acids to the trihaloacetic acids. Such carboxylic acids can be monocarboxylic acids, dicarboxylic acids or tricarboxylic acids, such as, for example, propionic acid, butyric acid, pivalic acid, succinic acid, citric acid or especially the very reasonably priced acetic acid. In the following embodiments, an excess of reactant/solvent mixture is always used for the reaction of sodium borohydride with trihaloacetic acids, so that clear solutions are formed. The minimal amount each of reactant/solvent mixture necessary for an industrial performance and its optimal composition must be determined in individual cases by preliminary experiments, as they are familiar to one skilled in the art.

The steroid to be converted—dissolved in an inert solvent—can be put into the sodium borohydride/- trihaloacetic acid reaction mixture thus prepared, which optionally contains another carboxylic acid. But purer process products are often obtained if this reaction mixture is put into a solution of the steroid. Normally, a reaction mixture produced from 2.5 mol to 20 mol of sodium borohydride is used per mol of steroid to be reacted. The reaction temperature is about −30° C. to +30° C. The optimal addition rate of the one component to the other must be determined by the preliminary tests familiar to one skilled in the art; too slow an addition rate is mostly not a drawback for the course of the reaction itself. The reaction time is generally 5 minutes to 120 minutes.

It is relatively not critical in which inert solvent the steroid to be reacted is dissolved. Suitable inert solvents are, for example, ethers, such as diethyl ether, diisopropyl ether, dioxane, tetrahydrofuran or 1,2-dimethoxyethane, chlorinated hydrocarbons such as methylene chloride, chloroform, carbon tetrachloride or liquid aromatic hydrocarbons, such as benzene, toluene or xylene.

The 3-oxo-4-ene steroid to be reacted of the general formula II can—as was already explained—have isolated or conjugated double bonds in 15-position, in 14- and/or 16-position, in the vinyl group of substituent $R_5$ or the vinylidene radical X and/or Z, and/or have a triple bond in substituent $R_5$ without these groupings being attacked in the reaction. 3-oxo-4-ene steroids with an etherified hydroxy group $R_4$ (preferably alkyl ether with 1 to 4 carbon atoms such as methyl ether, ethyl ether or tert-butyl ether) are not cleaved, but in the case of 3-oxo-4-ene steroids with an esterified hydroxy group $R_4$ (preferably alkanoyl ester with 1 to 6 carbon atoms, such as the acetate, propionate, pivalate or benzoyl ester) can be partially transesterified or reductively cleaved. In the case of 3-oxo-4-ene steroids, which carry halogen atoms (preferably fluorine or chlorine atoms), no halogen cleavage takes place during the reaction. 3-oxo-4-ene steroids with an oxo group in 17-position are reduced to the corresponding 17beta-hydroxy steroids, which, however, can be further oxidized without difficulty to the corresponding 17-oxo steroids, as is explained in one of the following embodiments.

The following embodiments are used to explain the invention in more detail.

EXAMPLES

EXAMPLE 1

220 mg of anhydrous sodium borohydride is added in portions with ice/water cooling to 2 ml of trifluoroacetic acid, 2 ml of glacial acetic acid and 2 ml of acetonitrile. Then, 288 mg of 17beta-hydroxy-4-androsten-3-one in 5 ml of dry methylene chloride is instilled, stirred at room temperature and carefully mixed after 30 minutes with saturated sodium bicarbonate solution. It is extracted with methylene chloride, washed neutral with water and dried on magnesium sulfate. The residue is chromatographed on a silica gel column by methylene chloride/methanol (99+1) and 240 mg of 4-androsten-17beta-ol of melting point 146°–149° C. is obtained.

EXAMPLE 2

370 mg of anhydrous sodium borohydride is added in portions with ice/water cooling to 5 ml of trichloroacetic acid and 5 ml of acetonitrile. Then, 500 mg of 17beta-hydroxy-4-androsten-3-one in 9 ml of methylene chloride is instilled. It is stirred at room temperature and is worked up after 30 minutes, as described in example 1. 400 mg of 4-androsten-17beta-ol with melting point 144°–147° C. is obtained.

EXAMPLE 3

570 mg of anhydrous sodium borohydride is added in portions with ice/water cooling to 5.5 ml of trifluoroacetic acid, 5.5 ml of glacial acetic acid and 10 ml of acetonitrile, so that the inner temperature does not exceed +10° C. After completion of the generation of hydrogen, the solution is instilled at room temperature in 274 mg of 17beta-hydroxy-4-estren-3-one in 5 ml of methylene chloride, stirred for 30 minutes and mixed carefully with saturated sodium bicarbonate solution. Then, it is extracted with methylene chloride, washed with water and dried on magnesium sulfate. After chromatographic purification of the crude product on silica gel with methylene chloride/methanol (99+1), 210 mg of 4-estren-17beta-ol of melting point 96°–99° C. is obtained.

EXAMPLE 4

800 mg of anhydrous sodium borohydride is added with ice/water cooling to 7 ml of trichloroacetic acid, 7 ml of pivalic acid and 10 ml of acetonitrile, so that the inner temperature does not exceed +10° C. The sodium borohydride solution is instilled at room temperature in 385 mg of 17beta-hydroxy-4-estren-3-one in 8 ml of methylene chloride. After 20 minutes, it is carefully mixed with saturated sodium bicarbonate solution and worked up as described in example 3. After chromatographing the crude product on silica gel with methylene chloride/methanol, 290 mg of 4-estren-17beta-ol of melting point 95°–98° C. is obtained.

EXAMPLE 5

Analogously to example 3, 300 mg of 17beta-hydroxy-18-methyl-4-estren-3-one is reacted with the reaction mixture produced from sodium borohydride. After chromatographic purification of the crude product on silica gel with hexane/ethyl acetate, 230 mg of 18-methyl-4-estren-17beta-ol of melting point 116°–117° C. is obtained.

EXAMPLE 6

Analogously to example 3, 500 mg of 17alpha-ethinyl-17beta-hydroxy-4-estren-3-one is reacted with the reaction mixture produced from anhydrous sodium borohydride. The crude product is recrystallized from acetone after treatment with activated carbon in acetone. Yield: 320 mg of 17alpha-ethinyl-4-estren-17beta-ol of melting point 160°–162° C.

EXAMPLE 7

Analogously to example 3, 350 mg of 17alpha-ethinyl-17beta-hydroxy-18-methyl-4-estren-3-one is reacted with the reaction mixture produced from anhydrous sodium borohydride. After chromatographing on silica gel with hexane/ethyl acetate, 240 mg of 17alpha-ethinyl-18-methyl-4-estren-17beta-ol of melting point 54° C. is obtained.

EXAMPLE 8

Analogously to example 3, 280 mg of 17alpha-ethinyl-18-methyl-17beta-hydroxy-4,15-estradien-3-one is allowed to react with the reaction mixture produced from sodium borohydride. The crude product is chromatographed on silica gel with hexane/ethyl acetate. Yield: 190 mg of 17alpha-ethinyl-18-methyl-4,15-estradien-17beta-ol of melting point 82° C.

EXAMPLE 9

Analogously to example 3, 830 mg of 17alpha-ethinyl-17beta-hydroxy-18-methyl-11-methylene-4-estren-3-one is reacted with the reaction mixture produced from anhydrous sodium borohydride. After chromatographing the crude product on silica gel with hexane/ethyl acetate and recrystallizing from hexane, 560 mg of 17alpha-ethinyl-18-methyl-11-methylene-4-estren-17beta-ol of melting point 110° C. is obtained.

EXAMPLE 10

Analogously to example 3, 680 mg of 17-phenyl-4,14,16-androstatrien-3-one is reacted with the reaction mixture produced from anhydrous sodium borohydride. After chromatographing on silica gel with hexane/ethyl acetate, 550 mg of 17-phenyl-4,14,16-androstatriene of melting point 97° C. is obtained.

EXAMPLE 11

Analogously to example 3, 930 mg of 18-methyl-17-phenyl-4,14,16-estratrien-3-one (melting point 191° C., produced analogously to 17-phenyl-4,14,16-estratrien-3-one (literature: E. Winterfeldt et al., Tetrahedron Letter, 27, 5833 (1986)) is reacted with the reaction mixture produced from anhydrous sodium borohydride. After chromatographing the crude product on silica gel with hexane/ethyl acetate, 730 mg of 18-methyl-17-phenyl-4,14,16-estratriene of melting point 93.5° is obtained.

EXAMPLE 12

Analogously to example 3, 360 mg of 17alpha-chloroethinyl-17beta-hydroxy-18-methyl-11-methylene-4-estren-3-one is reacted with the reaction mixture produced from anhydrous sodium borohydride. After chromatographing the crude product on silica gel with hexane/ethyl acetate, 230 mg of 17alpha-chloroethinyl-18-methyl-11-methylene-4-estren-17beta-ol of melting point 165° C. is obtained.

EXAMPLE 13

Analogously to example 3, 680 mg of 18-methyl-11-methylene-4-estren-3,17-dione is allowed to react with the reaction mixture produced from anhydrous sodium borohydride. The crude product obtained (600 mg) is reacted in 10 ml of acetone with 0.8 ml of an 8N chromium trioxide/sulfuric acid solution (Jones reagent). The reaction mixture is added to ice/water. The precipitated product is suctioned off, washed with water and dried. After chromatographing on silica gel with hexane/ethyl acetate and after recrystallizing from diethyl ether, 340 mg of 18-methyl-11-methylene-4-estren-17-one of melting point 98° C. is obtained.

We claim:

1. A process for the production of a 3-deoxy-4-ene steroid of formula I

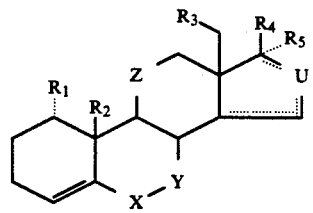

wherein
$R_1$, $R_2$ and $R_3$ are each a hydrogen atom or a methyl group,
$R_4$ is a phenyl group, a free hydroxy, an esterified hydroxy or an etherified hydroxy group,
$R_5$ is absent or is a hydrogen atom, a vinyl group or —C≡CR$_6$ wherein $R_6$ is a hydrogen atom, $C_1$–$C_4$-alkyl, or a halogen atom,
X is a methylene group, a fluoromethylene group, an ethylidene group of a vinylidene group,
Y and U are each a methylene group or an ethylidene group and
Z is a methylene group, an ethylidene group, a vinylidene group, a chloromethylene group or a hydroxymethylene group, and ⋯
represents three single bonds, one double bond and two single bonds, or a conjugated double bond,
said process comprising reducing a 3-oxo-4-ene steroid of formula II

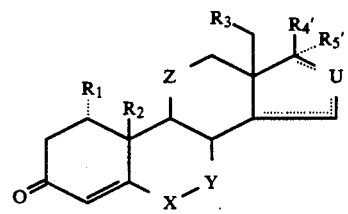

wherein ⋯
$R_1$, $R_2$, $R_3$, X, Y, Z and U have the meanings given above and
$R_4'$ and $R_5'$ are the same as $R_4$ and $R_5$, respectively, or together represent an oxo group,
with a reaction mixture of sodium borohydride, acetonitrile, inert solvent and
(a) trifluoroacetic acid and another carboxylic acid,
(b) trichloroacetic acid, or
(c) trichloroacetic acid and another carboxylic acid.

2. A process according to claim 1, wherein said 3-deoxy-4-ene steroid is a compound of formula Ia

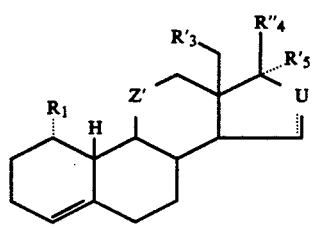

wherein ⋯
$R_3'$ is a hydrogen atom or a methyl group,
$R_4''$ is a hydroxy group or an alkanoyloxy group with up to 4 carbon atoms, $R_5''$ is a hydrogen atom, a vinyl group, an ethinyl group, a chloroethinyl group or a 1-propinyl group, $Z'$ is a methylene group or a vinylidene group, U is a methylene group, and is a single bond or a double bond.

3. A process according to claim 2, wherein said 3-deoxy-4-ene steroid is lynestrenol or desogestrel.

4. A process according to claim 1, wherein $R_4$ is free hydroxy.

5. A process according to claim 1, wherein said etherified hydroxy group of $R_4$ is an alkyl ether of 1-4 carbon atoms and said esterified hydroxy group of $R_4$ is an alkanoyl ester group of 1-6 carbon atoms.

6. A process according to claim 1, wherein acetonitrile is added to said reaction mixture to suppress foam formation.

7. A process according to claim 1, wherein said another carboxylic acid is a monocarboxylic acid, dicarboxylic acid or tricarboxylic acid.

8. A process according to claim 1, wherein said another carboxylic acid is selected from the group consisting of propionic acid, butyric acid, pivalic acid, succinic acid, citric acid and acetic acid.

9. A process according to claim 1, wherein said reaction mixture contains 2.5-20 moles of sodium borohydride per mole of 3-oxo-4-ene steroid.

10. A process according to claim 1, wherein the reaction temperature of said process is $-30°$-$30°$ C.

11. A process according to claim 1, wherein said inert solvent is selected from the group consisting of diethyl ether, diisopropyl ether, dioxane, tetrahydrofuran, 1,2-dimethyoxyethane, methylene chloride, chloroform, carbon tetrachloride, benzene, toluene and xylene.

12. A process according to claim 1, wherein $R_4$ is a phenyl group, a free hydroxy group, a $C_1$-$C_4$ alkyl ether of a hydroxy group or a $C_1$-$C_6$ alkanoyl ester of a hydroxy group, said another carboxylic acid is selected from the group consisting of propionic acid, butyric acid, pivalic acid, succinic acid, citric acid or acetic acid, and acetonitrile is added to said reaction mixture to suppress foam.

* * * * *